United States Patent [19]

Kelman et al.

[11] 4,093,861

[45] June 6, 1978

[54] GANTRY FOR COMPUTED TOMOGRAPHY

[75] Inventors: Arnold Lloyd Kelman, Waukesha; Thomas Eben Peterson, Greendale, both of Wis.

[73] Assignee: General Electric Company, Schenectady, N.Y.

[21] Appl. No.: 772,210

[22] Filed: Feb. 25, 1977

[51] Int. Cl.² .................... A61B 6/02; G01N 23/08
[52] U.S. Cl. .......................... 250/445 T; 250/490
[58] Field of Search .............. 250/445 T, 363 S, 523, 250/525, 490, 445 R, 521; 269/323, 289 MR, 289 R; 248/447, 143

[56] References Cited
U.S. PATENT DOCUMENTS

| | | | |
|---|---|---|---|
| 1,042,456 | 10/1912 | Manson | 269/289 MR |
| 1,389,068 | 8/1921 | Olson | 269/289 MR |
| 2,103,693 | 12/1937 | Pohl | 269/323 |
| 3,525,308 | 8/1970 | Koopmans | 269/323 |
| 3,922,552 | 11/1975 | Ledley | 250/445 T |

Primary Examiner—Alfred E. Smith
Assistant Examiner—T. N. Grigsby
Attorney, Agent, or Firm—Ralph G. Hohenfeldt

[57] ABSTRACT

An X-ray source and a detector array are mounted on opposite sides of a generally horizontally extending longitudinal axis of a rotating base. The rotating base is journaled on a tiltable frame. The frame is supported on curved tracks for tilting by translating along a curved path about a fixed transverse virtual axis of rotation which is perpendicular to and intersects the rotational axis of the rotating base. Tilting the frame permits making an X-ray scan through a layer of a patient which is at an acute angle relative to the longitudinal axis. The azimuth drive for the rotatable frame utilizes a toothed belt. A self-acting friction brake is provided for constraining the rocking base. A hoist is provided for making installation and removal of the X-ray source convenient.

3 Claims, 12 Drawing Figures

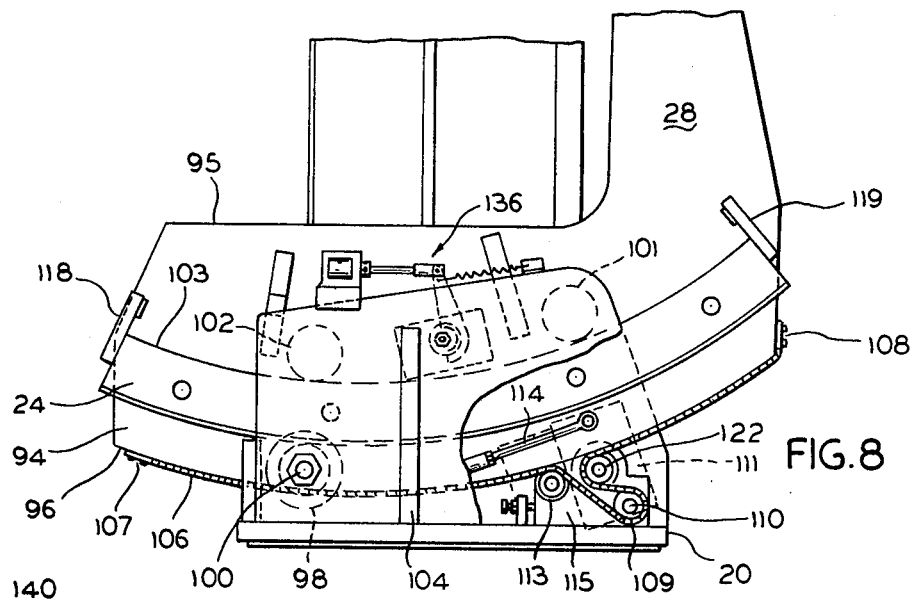
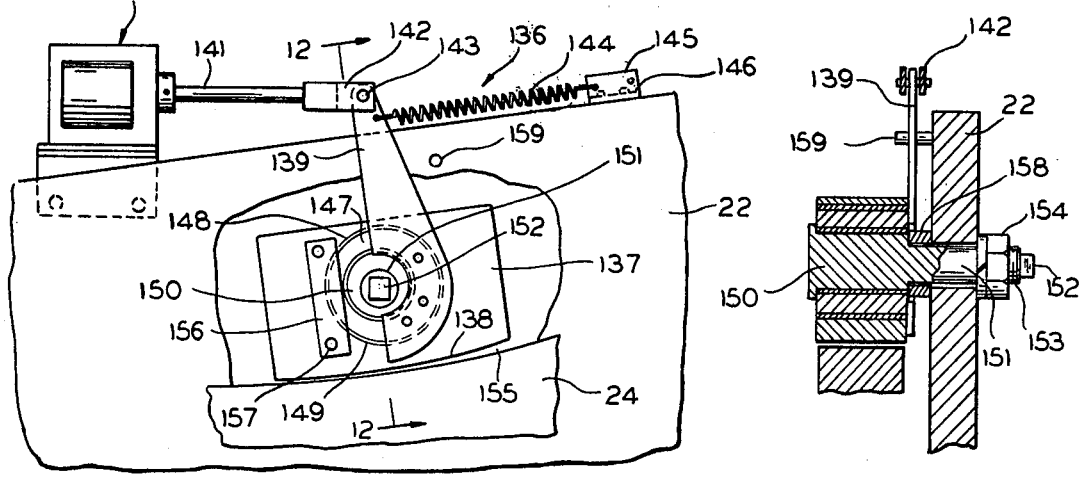
FIG.5      FIG.12
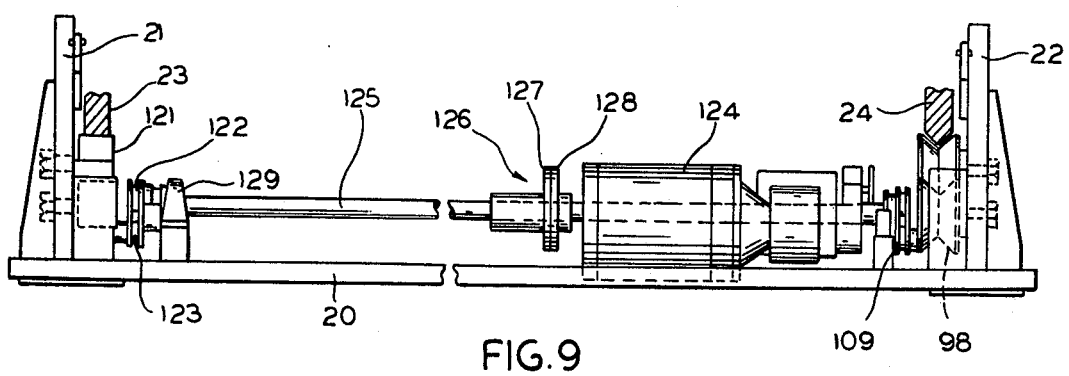
FIG.9

GANTRY FOR COMPUTED TOMOGRAPHY

BACKGROUND OF THE INVENTION

This invention relates to apparatus for performing computed X-ray tomography.

In one method of computed tomography, a patient is supported for being translated along a longitudinal axis which is usually horizontally disposed. The axis coincides with the center of rotation of a rotatable base which has an X-ray source on one side of the center of rotation and a multiple array of X-ray detectors on the other side. A fan-shaped X-ray beam, that is thin in the longitudinal direction, is projected through the patient as the base rotates so that the detectors may develop signals indicative of X-ray transmission characteristics along a plurality of paths through a subject undergoing examination. Analog signals representative of X-ray attenuation by all of the volume elements in a layer of the body at various rotational angles are then converted to digital signals which are used by a computer to produce signals which may be used for controlling a cathode ray tube to display a reconstructed image of the layer. Further background information on computed tomography is obtainable in an article entitled "Image Reconstruction From Projections" by Gordon et al; Scientific American, October 1975, Vol. 233, No. 4. A prior gantry appears in U.S. Pat. No. 3,922,522.

Another prior method of performing computed tomography involves jointly translating an X-ray source on one side of the body and a detector on the other side of the body across a body layer repeatedly and rotating the source and detector through a small angle for each translation.

In both of the foregoing examples, the X-ray beam is projected through a thin layer of the body so that the reconstructed layer is essentially perpendicular to the longitudinal axis along which the patient is translated to obtain views of successive layers. On some occasions, however, unique diagnostic information can only be obtained by viewing a slice or layer through the body which is tilted through a small vertical angle and is not perpendicular to the horizontal or longitudinal axis along which the patient is translated.

SUMMARY OF THE INVENTION

In accordance with the invention, the X-ray scanner is constructed and arranged for enabling taking views of body slices which are angulated relative to the longitudinal translational axis of the body but which are intercepted perpendicularly by the rotational or azimuth axis of the rotating base and the X-ray source and detectors orbiting therewith. More particularly, in a preferred embodiment of the invention, the rotatable base is supported on a main rocking frame which is adapted for rocking on curved segments or rocker tracks which are supported on rollers. The curvature of the rockers is generated from a transverse horizontal axis constituting a virtual center of rotation which is mutually perpendicular to the longitudinal axis of base rotation and a line coincident with the central ray between the X-ray source and detectors. Maintenance of this geometric relationship for any permissible tilt angle of the rotatable base permits simplification of the algorithm which the computer executes in connection with the image reconstruction process.

The terms X-ray and X-ray source are used herein for the sake of brevity and convenience but these terms should be construed as embracing gamma radiation and gamma sources and other penetrating radiation and sources as well. The apparatus just outlined is called a computed tomography gantry.

A primary object of this invention is to provide a gantry which enables taking angular slices or views of body layers in connection with a computed tomography procedure.

Another object is to provide a gantry wherein the rotatable base that rotates about a longitudinal axis and supports an X-ray source and detector for orbiting about a patient is supported on a frame for tilting by translating along a curved path defined by curved tracks and about a virtual laterally directed axis of rotation which is perpendicular to and intersects the longitudinal axis.

Another object is to achieve compactness and simplicity by coupling the rotatable base only at one side to the tilting frame means with a bearing that permits the rotatable base to be supported in cantilever fashion without suffering any angular or axial misalignment. A correlative of this object is to use a ball bearing that has a v-groove in the outer periphery of its inner race and a v-groove in the inner periphery of its outer race with the v-grooves opening toward each other and confining a single circumferentially disposed row of balls between them. The balls make four-point tangential contact with the sides of the v-grooves to thereby resist the stress of cantilever loading and the need to use only one row of balls results in an axially narrow bearing which contributes toward compactness.

How other foregoing and other more specific objects of the invention are achieved will be evident in the ensuing more detailed description of a preferred embodiment of the invention which will now be set forth in reference to the drawings.

DESCRIPTION OF THE DRAWINGS

FIG. 5 is a side elevation of a brake cooperating with a rocking member;

FIG. 8 is a side view, with parts broken away, of the lower portion of the rocking base;

FIG. 9 is a front view of the floor support and drive mechanism for the rocking base, with parts omitted for the sake of facilitating description;

FIG. 12 is a section of the brake taken along a line corresponding with 12—12 in FIG. 5.

DESCRIPTION OF A PREFERRED EMBODIMENT

Figure 1:
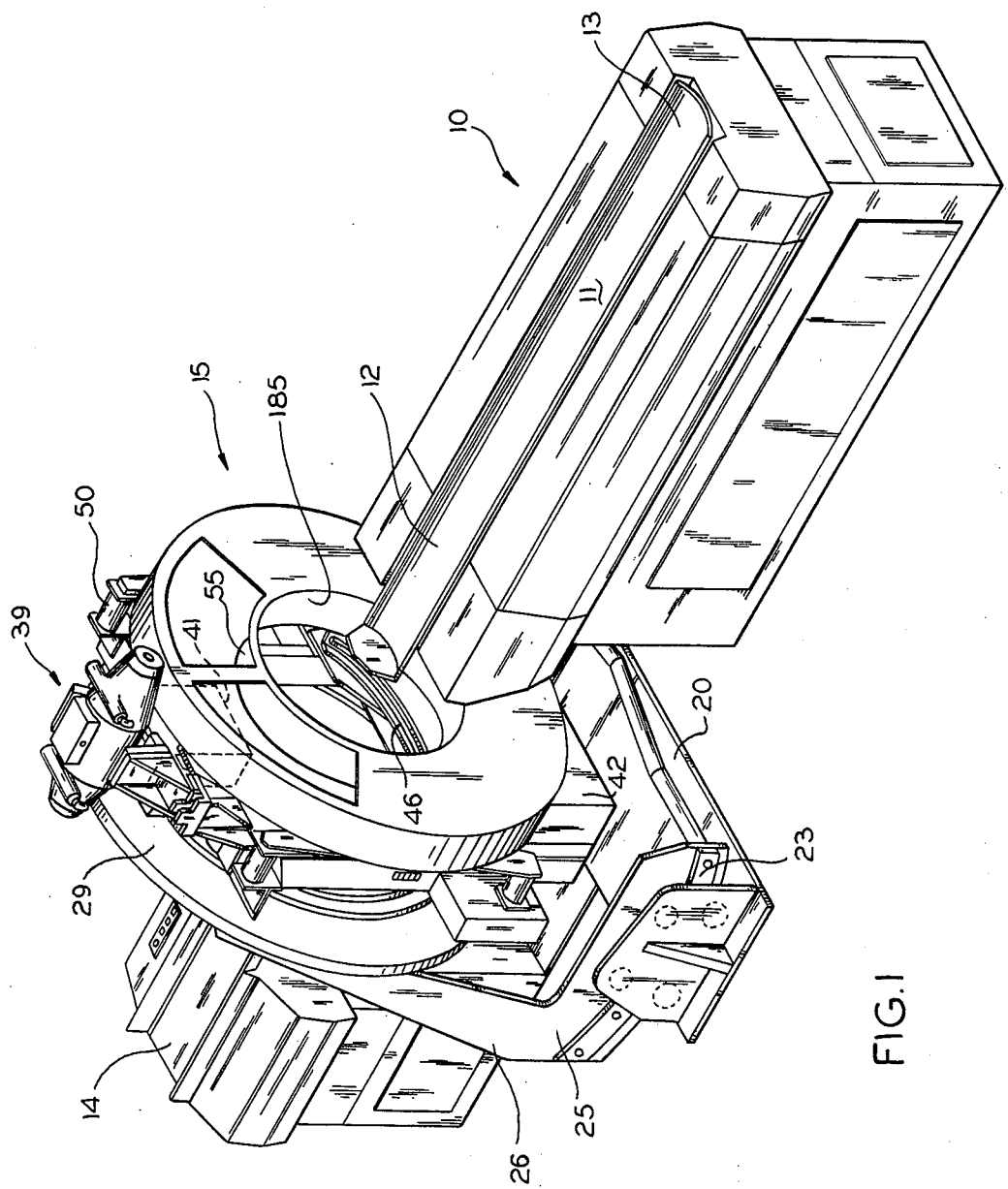
FIG. 1 is a perspective view of a computed tomography gantry, with its decorative shrouds removed, and an associated patient supporting table.
Figure 2:
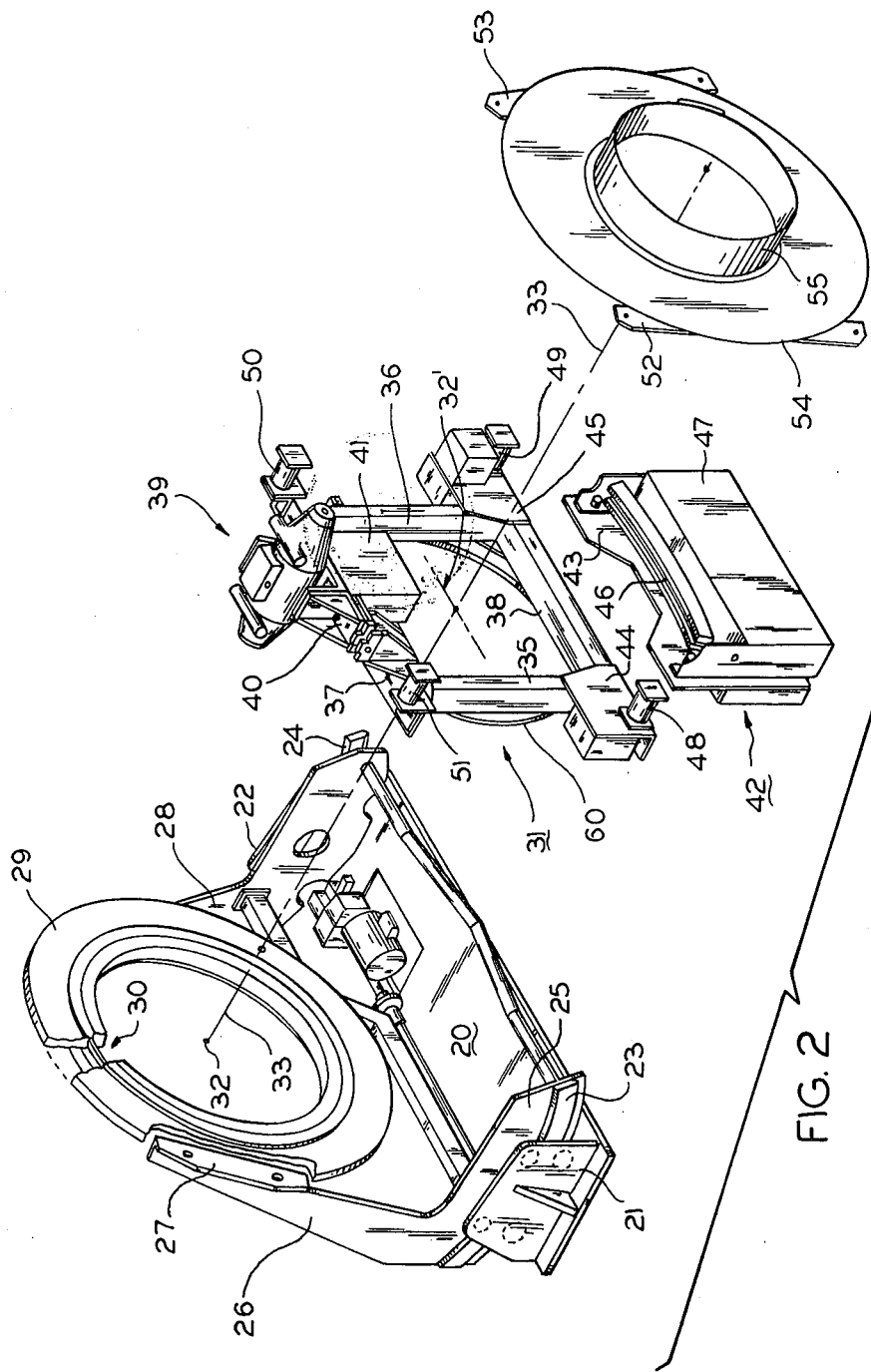
FIG. 2 is an exploded view of the gantry in the preceding figure.

The general features of apparatus for obtaining X-ray attenuation data for computed tomography will be outlined in reference to FIGS. 1 and 2. In FIG. 1, a table for supporting a patient undergoing tomographic examination is generally designated by the reference numeral 10. The table has a top 11 on which a patient may be supported in a recumbent position with the head at the end marked 12 and the feet at the end marked 13. Top 11 is translatable lengthwise which, in this discussion, is called the longitudinal direction. Top 11 is adapted for being translated longitudinally so that it extends in cantilever fashion from table 10 for the purpose of disposing successive longitudinally adjacent layers of a patient's body in the path of a scanning X-ray beam. The mechanism for advancing and retracting the patient longitudinally is within the housing of table 10 and is not shown in detail since it forms no part of the present invention.

Table top 11, when fully extended, obtains additional support from a rear table 14 so that substantially the entire length of a patient may be disposed in the scanning beam if desired.

X-ray scanning and obtaining X-ray attenuation data on a multitude of small volume elements in the body is carried out with components of a gantry which is generally designated by the reference numeral 15.

The principle elements of the gantry may be seen clearly in the FIG. 2 exploded view. The gantry comprises a floor base plate 20 with a pair of substantially identical upstanding plates 21 and 22 mounted at opposite ends. Plates 21 and 22 are equipped with rollers which will be described in detail later. The rollers support a tiltable frame comprising curved rocker tracks or segments 23 and 24. Tracks 23 and 24 are fastened to L-shaped members which are part of the tilting frame. One of the members is substantially completely visible in FIG. 2 and is seen to be a unitary member comprised of a generally horizontally extending base portion 25 and an upstanding leg portion 26. Typically, leg portion 26 is an edgewise disposed plate which has a laterally extending flat plate 27 fastened to it. Plate 27 and its counterpart on the other upstanding leg 28 are both fastened to a circular bearing or mounting plate 29 of the rocking frame. Thus, it will be evident that circular mounting plate 29, which is part of the tilting frame, may be rocked on rockers 23 and 24 to dispose the plane of plate 29 vertically if desired or at angles on opposite sides of vertical. The frame does not rock in the manner in which the rockers of a chair would rock on a flat floor. In such case the center of curvature of the rockers translates. In the present design, the curved rocker tracks, cooperating with the rollers, results in the rocker tracks translating along a curved path having radii extending back to a virtual axis of rotation which does not translate even though the frame supported on the rockers tilts.

Plate 29 of the tiltable frame is provided with a large ring bearing structure 30 to which rotatable base 31 is mounted. The center of rotation of rotatable base 31 and bearing structure 30 is marked 32 and the axis of rotation, herein called the longitudinal axis, is shown as a dashed line and is marked 33. Axis 33 is also commonly called the azimuth axis. A transverse horizontal line 32' extending through point 32 constitutes a virtual axis about which support plate 29 and bearing 30 which it carries tilt through opposite vertical angles on rockers 23 and 24. In a commercial embodiment, the plane of circular plate 29 is adapted to be tilted rearwardly or cranially and forwardly or caudally about said transverse virtual axis through angles of minus and plus 15° relative to vertical. This means that longitudinal axis 33 may be tilted upwardly or downwardly through a corresponding acute angle.

Rotating base 31 is mounted to bearing structure 30 for rotation thereon about longitudinal axis 33. In general terms, rotating base 31 has a frame comprised of side members 35 and 36, a top cross member 37 and a bottom cross member 38. An X-ray tube casing 39 is mounted to cross member 37 by means of a bracket assembly 40 which permits lateral and longitudinal position adjustment of the X-ray tube casing for causing the central ray of the X-ray beam emanating from the X-ray source to pass through the longitudinal rotational axis 33.

Mounted to the output side of X-ray source 39 is a collimator device 41 which, in this particular design, collimates the X-ray beam into a thin fan-shaped beam which originates from a substantially point source on the target of an X-ray tube in casing 39. In a commercial embodiment, by way of example, the longitudinal thickness of the X-ray beam is about 1 cm and a slice or layer of corresponding thickness in the body is penetrated by the beam for each scan.

An X-ray detector and data acquisition assembly 42 is mounted to rotatable base 31. This assembly comprises a plate 43 whose corners are fastened to plates 44 and 45 which extend from the base. The detector portion has a curved X-ray input window 46 behind which there is an array of adjacent detector cells, not visible, which each produce output signals corresponding with the intensity of the plurality of rays that radiate from the X-ray source and penetrate contiguous series of volume elements in a body layer that is disposed along longitudinal axis 33 during X-ray examination of a body. The discrete plurality of analog signals, representative of X-ray attenuation by small volume elements in the body, are processed in a data acquisition system within an enclosure 47 after which the analog signals are converted to digital signals which are used by a computer, not shown, to execute the image reconstruction algorithm. A suitable detector is shown in a copending application, Ser. No. 727,260, filed Sept. 27, 1976, and assigned to the assignee of this application.

In further reference to FIG. 2, rotatable base 31 has four forwardly extending posts or spacers 48–51 to which a pair of flat bars 52 and 53 are mounted. A disc 54 having a central hole surrounded by a cylindrical tube 55 is carried by bars 52 and 53 and serves as the rear wall of a cylindrical chamber 55, see FIG. 1, in which electric cables are wrapped that are used to make electrical connections with the X-ray tube 30 and data acquisition system 42.

Figures 6, 7:
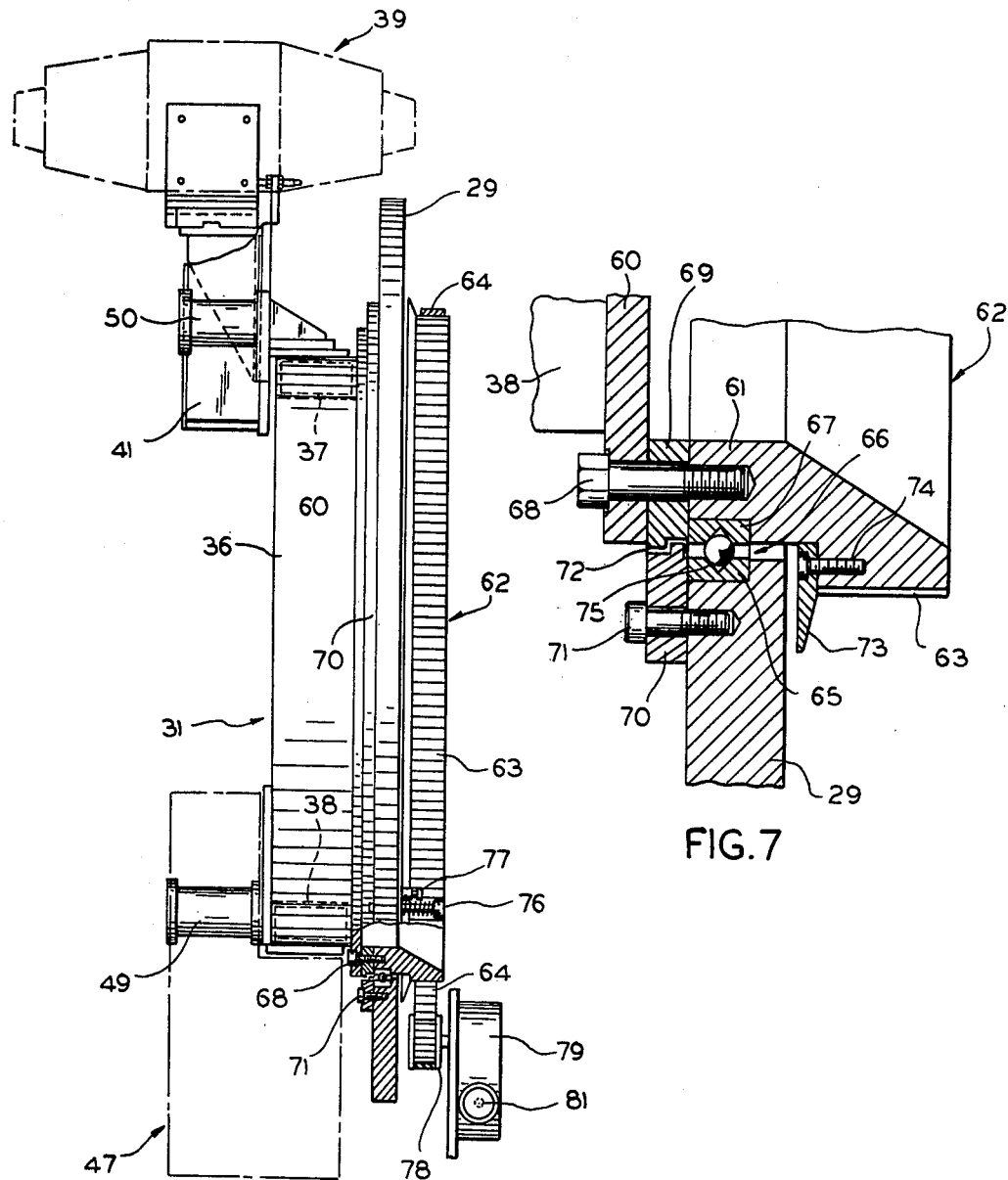
FIG. 6 is a side elevation of the rotatable base with parts broken away and other parts shown in sections to illustrate the bearing with which the rotatable base is journaled to the rocking frame.
FIG. 7 is an enlargement of a fragment of the bearing structure with some parts being shown in sections.

The manner in which the rotatable base 31 is journaled for rotation on circular support plate 29 of the tilting frame will now be discussed in reference to FIGS. 6 and 7 primarily. Note in FIG. 6 that the frame of base 31 comprised of side members 35 and 36 and top and bottom members 37 and 38 is fastened to an apertured plate 60 which is also visible on rotatable base 31 in FIGS. 2 and 7. The frame comprised of members 35–38 supports X-ray tube casing 37, collimator 41 and the detector and data acquisition system 42. In FIG. 7 it is evident that plate 60, to which the frame members 35–39 are fastened, is also fastened to the rim 61 of a pulley 62 which has external teeth 63 for being engaged by an internally toothed closed loop drive belt 64. In FIG. 7, the mounting ring 29 which, as may be seen in FIGS. 1 and 2, is supported from the upright legs 26 and 28 of the curved tracks or rockers, has a counterbore into which the outer race 65 of a ball bearing 66 is pressed. The inner race 67 of the ball bearing is pressed into a counterbore in the rim of pulley 62. Plate 60 of the rotatable base is fastened to the rim of pulley 62 with circumferentially spaced machine screws such as the one marked 68 and there is an intervening ring 69 between plate 60 and the pulley rim which retains the inner race 67 of the bearing in the rim. Another ring 70 is fastened to support ring 29 with circumferentially arranged machine screws such as the one marked 71 which clamp the outer race 65 of the bearing to ring 29. There is a gap 72 between retaining rings 69 and 70. Hence, plate 60 and pulley 62 are essentially unitary and rotatable in circular plate 29 which is supported for rocking as was mentioned earlier. Thus, the X-ray tube casing 39 and data acquisition system 47 being mounted on plate 60 will orbit an examination body disposed along axis 33 when pulley 62 is driven rotationally. Note that pulley 62 is provided with a beveled ring flange 73 which is secured to the rim of the pulley 62 with machine screws 74. Flange 73 serves to prevent the belt 64 from sliding axially off of pulley 62.

Note also in FIG. 7 that a bearing 66 is used which has v-shaped grooves 75 in the inner and outer races 65 and 67. This type of bearing is especially efficient in maintaining alignment between the inner and outer races when the bearing is subjected to a cantilever load as is the case here where heavy components such as the X-ray tube casing 37, data acquisition system 47 and the supporting frame comprised of members 35–38 are mounted to ring 60 which is, in turn, carried exclusively on the inner race 67 of the bearing.

Note in FIG. 6 that a spring biased detent 76 is provided for selectively interlocking pulley 62 with circular support plate 29. A locking device 77 is also associated with the detent for holding it out of engagement with circular plate 29. The detent is normally disengaged so that the pulley may be driven by belt 64 but the detent may be engaged when it is desired to interlock the pulley and circular plate 29 such as during shipping the machine, or when the belt 64 is removed, or when normal balancing of the rotatable base would be upset by removal of one of the parts that is supported on the base.

Referring to FIG. 6, the rotatable base 31 which carries the X-ray tube casing 39 and data acquisition assembly 47 is rotated in circular plate 29 with belt 64. The belt is driven with a pulley 78 which is fastened to the shaft of a speed reducer 79. The motor 80 for driving the speed reducer has been omitted from FIG. 6 but its shaft 81 is shown in that figure. The drive assembly is visible in FIG. 10 which is a rear view of the gantry. In this view it may be seen that motor 80 and speed reducer 79 are mounted on a vertically disposed base plate 82. Base 82 is supported at one end in a cantilever fashion with some vertically yieldable support members 83 which are shown schematically and are mounted to the upstanding leg portion 26 of one of the rocking supports. Base 82 has a pair of idler pulleys 84 and 85 mounted for rotation on it. These pulleys serve to maintain belt 64 in contact with most of the periphery of pulley 62. Base plate 82 is urged to rotate counterclockwise about its end support 83 under the influence of some springs 86 which are shown schematically. The tendency for the base plate to swing down results in the tension on the belt 64 being maintained and the arrangement also introduces some resiliency into the drive so the vibration will not be felt when it is started and stopped suddenly. The mounting is such that if the belt 64 should break, base 82 will remain supported in cantilever fashion.

Motor 80 is reversible. It is controlled to drive rotatable frame 31 and the X-ray tube and detector which it carries from 0° to 360° and from 360° back to 0°.

A more detailed discussion of how the gantry is adapted for enabling the X-ray scanner to be rocked cranially and caudally to enable obtaining a view of a slice of the body which is at a small vertical angle relative to horizontal will now be discussed in greater detail in reference to FIGS. 2, 3, 4 and 8–11.

As stated earlier, circular plate 29 is part of a tiltable frame in which the bearing for rotating base 31 is mounted. The frame is comprised of a pair of members which are designated generally by the reference numerals 26 and 28. One of the members, 28, will be described in detail. Refer to FIG. 4. Member 28 is generally L-shaped and has an upstanding leg portion 90 to which a flange 91 is welded. Flange 91 is used for fastening the upstanding leg of member 28 to circular plate 29 such as with machine bolts 92 and 93. The member has a substantially horizontally extending base portion 94 which has a straight top edge 95 and a curved bottom edge 96. The curved rocker segment or track 24 is bolted to the side of base 94. As can be seen in FIG. 9, in particular, track 24 has a v-shaped lower edge. This v-shaped edge runs in a pair of rollers 98 and 99 which each have a v-groove in their periphery. Rollers 98 and 99 are journaled on stud shafts such as 100 which are held by means of nuts to upstanding plate 22 which is supported from base 20. As can be seen in FIG. 8, there are some cylindrical blocks 101 and 102 fastened to the inside of upstanding plate 22 and these blocks almost touch the curved upper edge 103 of rocker segment 97. Their primary purpose is to assure that track 24 cannot pull out of grooved rollers 98 and 99 under any circumstances. Upstanding plate 22 has a web 104 welded to it and to base plate 20 to stiffen plate 22 and assure that it does not tend to flex outwardly. The upstanding plate 21 on the opposite side is similarly stiffened with a web 105, see FIG. 3. Plate 22 must be very rigid since any flexure would result in the center of rotation 32 of the rotatable frame 31 shifting which would be detrimental to getting reproducible X-ray attenuation data incidental to having the X-ray tube and detector orbit around a patient who is coincident with axis 32.

Since plate 22 is rigid and since the track 24 cannot shift laterally because of its v-shaped lower edge running in a v-groove of rollers 98 and 99, a vertical plane through the v-grooves constitutes a reference plane for all lateral adjustments which must be made to establish axis 32 at a fixed point relative to the patient support table. The curvature of track 24 is such that the center from which it is generated is on a transversely extending line which intersects longitudinal axis 32. Thus, the transverse axis is essentially a virtual axis for a curve along which the rocker translates. The point of intersection of the virtual transverse axis of the tracks and the longitudinal axis 32 remains fixed in space even though the mechanism is tilted on the tracks.

Each of the rockers 26 and 28 is driven. As can be seen particularly well in FIG. 8, the drive mechanism on the side of the tilting frame having rocker 28 comprises a chain 106 which is fastened at its opposite ends 107 and 108 to the curved bottom edge 96 of the rocker base 94. The chain is engaged by a drive sprocket 109 on a shaft 110. A plate 111 is journaled on shaft 110. This plate carries an idler sprocket 112 and there is another idler sprocket 113 carried by a bracket 115. Idler sprockets 112 and 113 maintain chain 103 in contact with almost all of the length of the curved lower edge 96 of rocker portion 94. Plate 111 is adjustable angularly with a turnbuckle assembly 114 which enables the chain 106 to be tensioned by swinging sprocket 112 in one direction or the other as required. Bracket 115 is also adjustable with a jack screw 116.

Fastened to the opposite ends of curved rocker track 24 are a pair of stops 118 and 119 which strike cylindrical blocks 101 and 102 to prevent the rocker tracks from going to far in either direction. As indicated earlier, in this example, the amount of forward or rearward tilt from vertical is about 15° but more or less tilt may be desired in some cases. In reality, the plane of the fan-shaped X-ray beam tilts to a vertical angle corresponding with that of the rocker frame measured from a vertical plane extending through the virtual axis of tilting and the plane of a slice in the body from which X-ray attenuation data is being taken.

The opposite support leg 26 also has a curved track 23 fastened to its side. This track may be seen in section in FIG. 10 and it is also apparent in the left bottom region of FIG. 3. This track runs on a pair of flat periphery rollers such as the one marked 121 in FIG. 10. Since the curved bottom edge of curved track 23 is flat as compared with the bottom edge of rocker 24 on the other side which is v-shaped, rocker 23 may shift axially on rollers 121 so that there need be no concern about alignment of this track and its rollers since, as was explained earlier, the reference line for rotational center 32 is the vertical plane which is coincident with the tip of the v-shaped rocker edge. The lower curved edge of L-shaped leg 26 of the tilting frame also has a chain, similar to chain 106, for tilting it. The sprockets 122 and 123 for driving this chain are visible in FIG. 9 where the drive motor 124 is also depicted. The drive motor shaft is connected to a drive shaft 125 with a coupling 126. This coupling is made in sections 127 and 128 which are relatively rotatable to permit phasing of each of the chain drives so that tilting occurs without distortion of the frame. Drive shaft 125 is supported in pillow blocks 129 and 130 as can be seen particularly well in FIG. 10.

Figure 3:
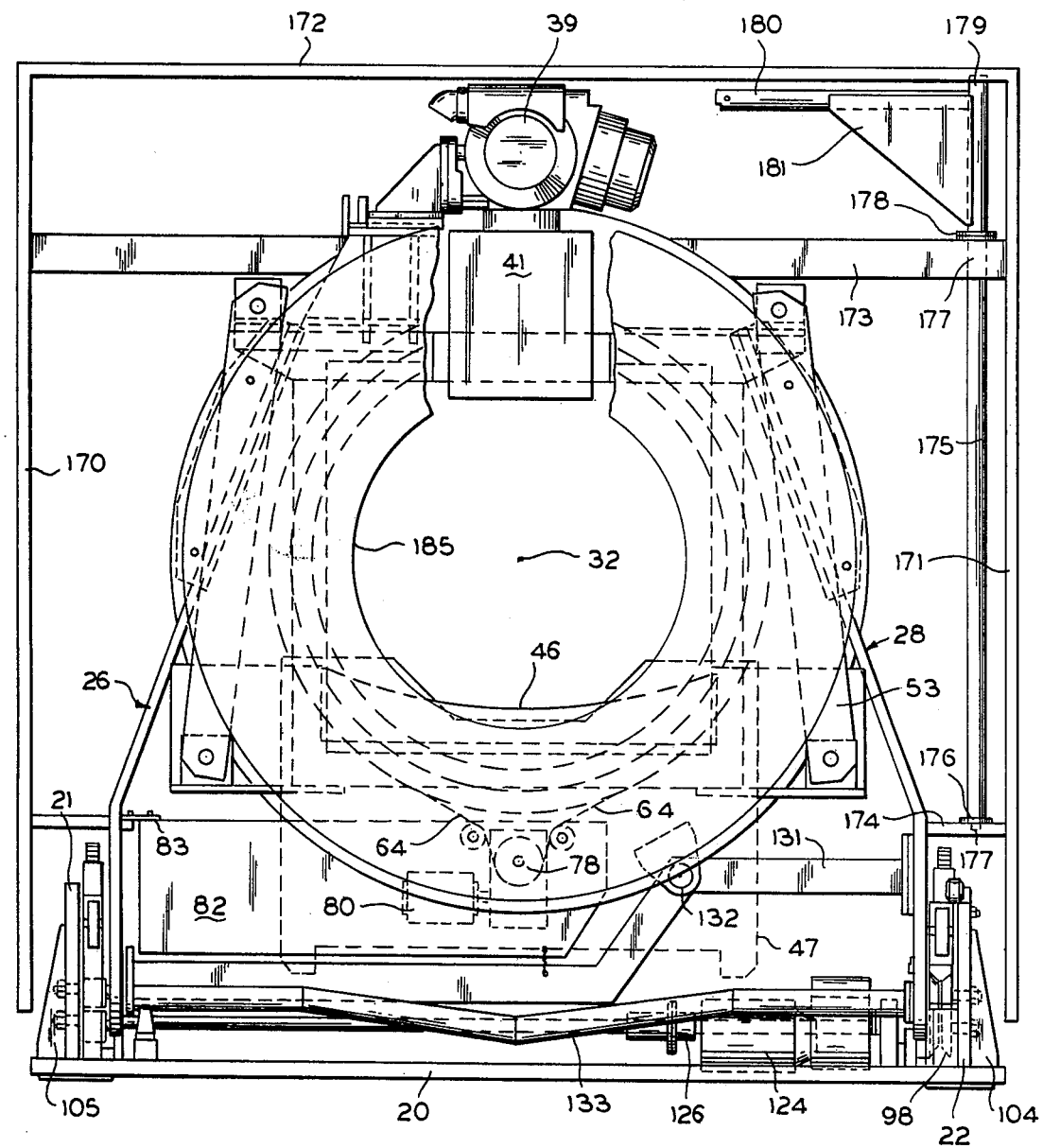
FIG. 3 is a front elevation of the gantry in FIG. 2 wherein the rotatable base is assembled to the rocking frame and showing the frame for supporting the decorative shrouds and a hoist jib adjacent the mechanism.
Figure 4:
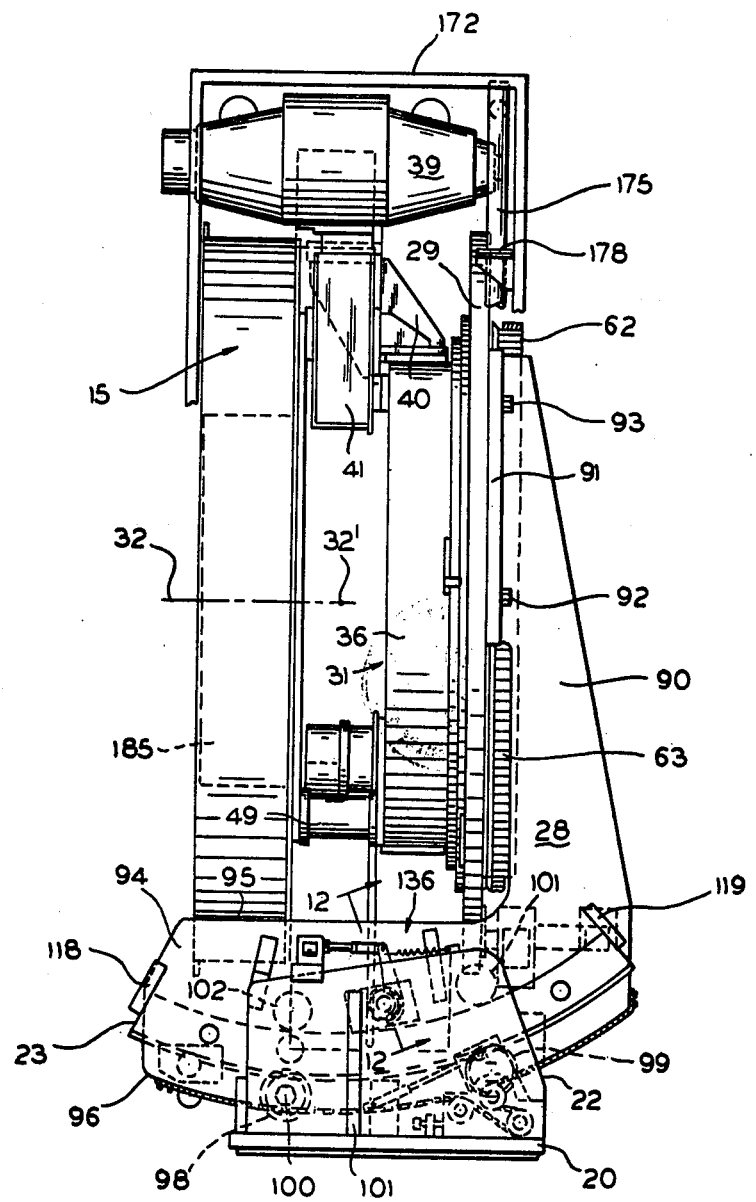
FIG. 4 is a right side elevation of the apparatus shown in FIG. 3 with some parts being shown fragmentarily.

The leg assemblies 26 and 28 constituting parts of the tilting frame, as can be seen in FIG. 3, are tied together with a cross brace 131 which also connects through a bracket 132 to ring 29. There is another cross member 133 for further stiffening the assembly.

In the illustrated preferred embodiment, the curved tracks 23 and 24 are on the tilting frame and the rollers supporting them are on the stationary stands 21 and 22. However, those skilled in the art will appreciate that the rollers could be on the tilting frame and the tracks could be on the stands 21 and 22. Either way the tilting motion of the frame would occur along a curved path about a virtual transverse axis.

The tilting frame is provided with unique brakes one of which is generally designated by the reference numeral 136 and which will now be described primarily in reference to FIGS. 4, 5 and 12. In FIG. 5, it is evident that the brake comprises a rectangular metal block which serves as a brake shoe 137. The shoe has a lower curved face 138 which is adapted to frictionally engage the upper curved surface of track 24. The brake is actuated with a lever 139. A solenoid operator 140 is used to disengage the brake. A rod 141 extends from the armature of the solenoid and terminates in a clevis 142 which pivotally connects with lever 139 by means of a pin 143. When solenoid 140 is energized, lever 139 is urged to the angular position in which it is shown such that friction surface 138 of brake shoe 137 is in spaced relationship with track 24 so no braking action occurs. When solenoid 140 is deenergized, lever 139 is urged clockwise through a small angle by a coil spring 144 which has one of its ends connected to lever 139 and the other of its ends attached to a bracket 145. This bracket is held by means of screws 146 to the upstanding roller support plate member 22. Unless solenoid 140 is energized, spring 144 will cause the lower surface 138 of brake shoe 137 to frictionally engage track 24.

Brake shoe 137 is actuated with an eccentric device comprised of a cylinder 147 which is rotatable in a bushing or bearing 148. Bushing 148 is fixed in brake shoe 137. Offset from the center of cylinder 147 is another bushing 149 which is fixed in the cylinder. Another shaft 150 is rotatable in bushing 149. Shaft 150 has an integral axial shaft extension 151 whose center is eccentric to the center of shaft 150. Shaft extension 151 has an end portion 152 which is square in cross section to facilitate engaging it with a wrench to effect rotation of cylindrical shaft 150. As is evident in FIG. 12, shaft extension 151 has a threaded portion 153 immediately adjacent square end portion 152. A nut 154 is turned onto threads 153 for supporting shaft 150 and its extension 151 in upstanding plate or stand 22. When shaft 150 is rotated about the axis of shaft extension 151 by engaging square end portion 152 with a wrench, shaft portion 150 is caused to swing eccentrically and, hence, raise or lower brake shoe 137. This enables setting the gap 155 between brake surface 138 and the top of rocker track 24 small so that brake shoe 137 needs to travel only a small distance to frictionally engage and disengage with track 24. When the brake shoe has been adjusted, nut 154 is tightened so that there will be no rotation of shaft extension 151 in upstanding plate 22. Lever 139 is fastened to cylinder 147 so that when the lever is rotated through a small angle as described above, the cylinder will turn on shaft 150, which is eccentric to cylinder 147, to thereby move shoe 137 downwardly to frictionally engage the shoe with the top of track 24. The cylinders or shafts are retained in shoe 137 with a thin strap 156 which is secured with screws 157 to shoe 137. A collar 158 spaces shaft 150 from plate 22 so there is clearance for the lever 139 to swing. A stop pin 159 limits the distance through which lever 139 can swing under the influence of spring 144.

Figure 10:
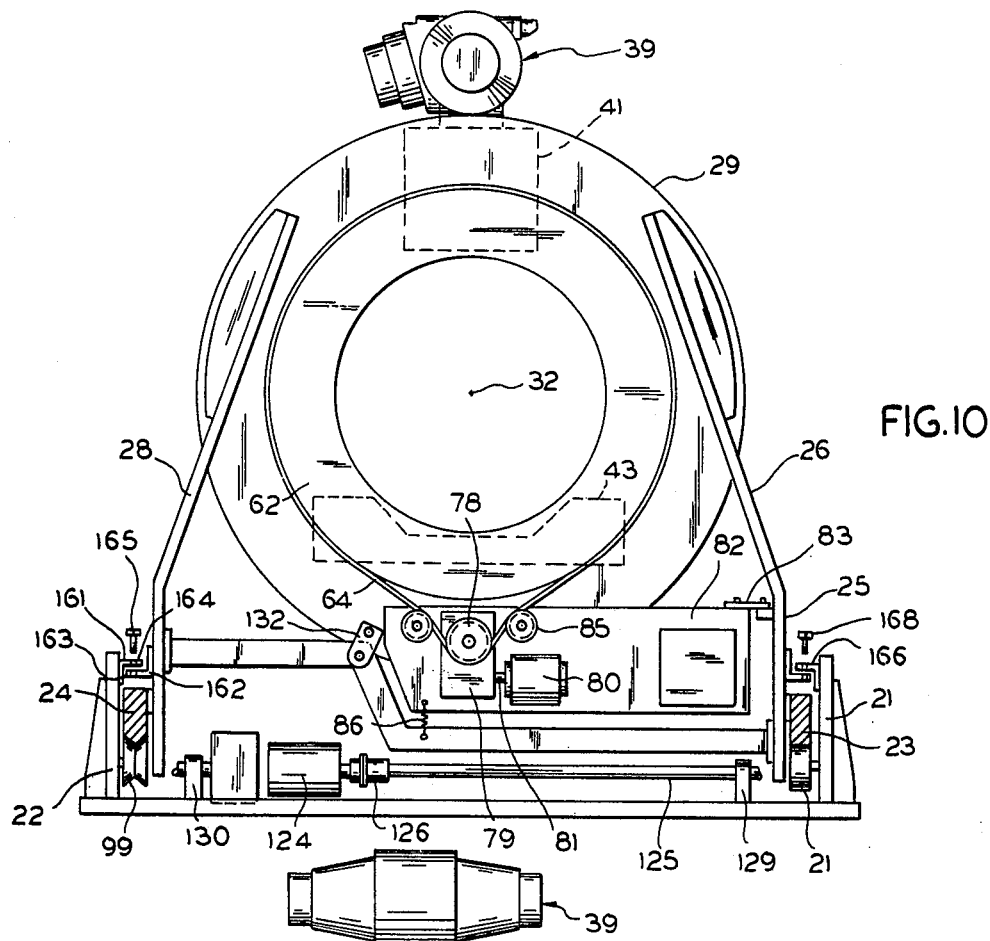
FIG. 10 is a rear view of the gantry with some parts omitted.
Figure 11:
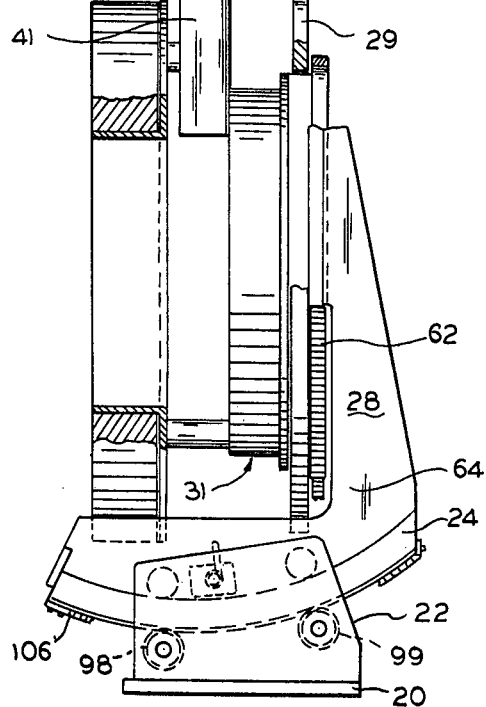
FIG. 11 is a side view of the gantry similar to FIG. 4 but with some parts omitted.

Referring to FIG. 10, one may see that the gantry is provided with means for lifing the tracks 24 and 23 from the rollers such as 99 and 121, respectively, on which the tracks are supported. The lifting means are also effective to prevent the L-shaped frame members 26 and 28 from rocking on the rollers. As can be seen in FIG. 10, the lifting and locking means comprise a pair of angle brackets 161 and 162. Bracket 161 is fixed to upstanding plate 22. Bracket 162 is fixed to L-shaped member 28. As shown, there is a space between brackets 161 and 162 and the track 24 is resting on v-grooved rollers 99. The respective brackets have holes 163 and 164 which are aligned with each other. When it is desired to lift track 24, for example, from its rollers 98 and 99 and to lock L-shaped member 28 to upstanding plate 22, a bolt 165 is inserted through holes 163 and 164. A nut, not shown, is then tightened onto bolt 165 in which case the bolt acts like a jack and lifts L-shaped member 28 and everything that is attached to it. The other side of the apparatus is provided with a similar pair of angle brackets 166 and 167 through which a bolt 168 is inserted for effecting jacking as previously described. The jacking or lifting devices are used when the machine is being shipped to prevent inadvertent tilting of the frame and to avoid having rely exclusively on brake 137 to prevent tilting.

Another important feature of the new gantry is a built-in jib on which a hoist, not shown, may be mounted for handling the X-ray tube casing 39 or the data acquisition unit 42 if these devices or any other devices must be removed from rotating base 31 in connection with maintenance and repair procedures. The jib may be seen best in FIG. 3 which shows the gantry as it appears from the front. In this figure a frame is mounted to the L-shaped members 26 and 28. The frame comprises side members 170 and 171 and a top member 172. Panels, not shown, for concealing the mechanism are mounted to this frame. The frame has an upper internal cross member 173 and a lower laterally extending member 174. The jib for the hoist constitutes a column, which in this case is a metal tube 175. Tube 175 has a flange or collar 176 at its bottom end. A shaft 177 extends below the collar into a corresponding opening in cross member 174, thus enabling rotation of column 175 about its axis. The column is also journaled at 177 in cross member 173. The column has another load bearing flange 178 and an extension 179. A horizontally extending arm 180 is fastened to extension 179 by a pair of gussett plates such as 181. Plate 181 may be suitably welded to extension 179 and arm 180. Although the cross section of arm 180 is not visible, it is essentially a channel whose sides are bent inwardly to define a slot that is coextensive with the length of the arm 180. The channel is for accommodating a roller carriage, not shown, to which a sling may be attached for engaging with X-ray tube casing 39 or data acquisition assembly 46, for example, when it is desired to remove or reinstall these heavy components. In such cases, rotating base 31 may be rotated until whatever component is to be engaged is under arm 180 at which time it may be engaged with a sling. The device may then be moved clear of the gantry by swinging arm 180 about the axis of column 175.

In FIG. 4 the cylindrical shell 15 for enclosing the cables is visible in profile. This shell, as can be seen in FIG. 4 and in FIGS. 1 and 3, has a central opening 185 through which the patient undergoing examination may be passed by translation of patient supporting table 11. In FIG. 4 the rotational axis for the rotating base 31 which carries the X-ray tube casing 39, collimator 41 and the data acquisition system 46 is marked 32 as it is in FIG. 1. The horizontal axis 32', as indicated earlier, is the axis from which the curvatures of tracks 23 and 24 are generated. The fan-shaped X-ray beam emerging from collimator 41 passes through intersecting axes 32 and 32'. Thus, axis 32' constitutes a virtual axis for tilting or inclining rotatable base 31. There is no shift of the X-ray beam relative to axis 32' when the frame is tilted by rocking of L-shaped segments 26 and 28. Thus, the slice or layer of interest to which horizontal axis 32 is always perpendicular when the frame is upright or tilted can always be determined precisely.

Although several features of the new gantry have been described in considerable detail, such description is intended to be illustrative rather than limiting, for the new features may be variously embodied and are to be limited only by interpretation of the claims which follow.

We claim:

1. X-ray tomographic apparatus comprising:

frame means and means for supporting said frame means for movement along a curved path about a laterally directed virtual axis to thereby enable said frame means to be tilted between opposite angles with respect to vertical, means for driving said frame means along said curved path to thereby effect tilting of said frame means about said virtual axis of rotation, ball bearing means having an outer race supported from said frame means and having an inner race and a plurality of balls between said races, said bearing means having a center of rotation about a longitudinal axis that is perpendicular to said laterally directed virtual axis, said outer race being fixed to said frame means, said inner race having a single v-shaped groove encircling its outside periphery and said outer race having a single v-shaped groove encircling its inside periphery, said grooves being presented toward each other for confining said plurality of balls, rotatable base means, X-ray source and X-rays detector means mounted on said rotatable base means on opposite sides, respectively, of said longitudinal axis for jointly orbiting about said longitudinal axis, pulley means coupled to said inner race and said rotatable base means being fastened to said pulley means, said pulley means and base means having aligned central openings for enabling an examination body to be disposed along said longitudinal axis in the path of the beam from said X-ray source, and motor means and means for supporting said motor means on said frame means and means for coupling said motor means in driving relation with said pulley means.

2. X-ray tomographic apparatus comprising:

frame means mounted for movement along a curved path about a laterally directed virtual axis to thereby enable said frame means to be tilted between opposite angles with respect to vertical, stationary support means spaced from each other in the lateral direction at opposite sides of said frame means, a pair of curved tracks disposed downwardly convexly at opposite sides of said frame means, respectively, and mounted on one of said frame means and said stationary support means, the radii of curvature of said tracks passing through said virtual transversely directed axis, roller means at opposite sides, respectively, of said frame means and supported for rotation on the other of said frame means and said stationary support means for cooperating with said tracks, one of said tracks having an edge that is substantially v-shaped in cross section and the roller means with which said track cooperates have peripheral grooves which are substantially v-shaped, the other of said tracks having an edge that is substantially flat and the roller means with which said other track cooperates have peripheries which are substantially flat, rotatable base means supported for rotation relative to said frame means about a longitudinal axis which is perpendicular to and intersects said laterally directed virtual axis, X-ray source and X-ray detector means mounted on said rotatable means on opposite sides, respectively, of said longitudinal axis for jointly orbiting about an examination body which may be disposed along said longitudinal axis, means for driving said frame means along said curved path to thereby effect tilting of said frame means about said virtual axis of rotation, and means for driving said base rotatably.

3. The apparatus as in claim 2 wherein:

it is a lower edge of one of said curved tracks which has v-shaped cross sectional configuration and the rollers on which said track runs have peripheral grooves, respectively, and it is the lower edge of the other of said curved tracks which is flat and the rollers on which said last named track runs have flat peripheries.

* * * * *